(12) United States Patent
Frazer

(10) Patent No.: US 8,927,063 B2
(45) Date of Patent: Jan. 6, 2015

(54) COMPOSITIONS FOR THE TREATMENT OF TIMBER AND OTHER WOOD SUBSTRATES

(75) Inventor: Frank William Frazer, Auckland (NZ)

(73) Assignee: TimTechChem International Limited, Wairau Valley (NZ)

( * ) Notice: Subject to any disclaimer, the term of this patent is extended or adjusted under 35 U.S.C. 154(b) by 109 days.

(21) Appl. No.: 13/133,980

(22) PCT Filed: Dec. 11, 2009

(86) PCT No.: PCT/NZ2009/000285
§ 371 (c)(1),
(2), (4) Date: Aug. 29, 2011

(87) PCT Pub. No.: WO2010/082840
PCT Pub. Date: Jul. 22, 2010

(65) Prior Publication Data
US 2011/0300302 A1 Dec. 8, 2011

(30) Foreign Application Priority Data

Dec. 12, 2008 (NZ) .......................................... 573574

(51) Int. Cl.
| | | |
|---|---|---|
| *B05D 7/06* | (2006.01) | |
| *A01N 25/02* | (2006.01) | |
| *B27K 3/00* | (2006.01) | |
| *B27K 3/50* | (2006.01) | |

(52) U.S. Cl.
CPC ........ *A01N 25/02* (2013.01); *B05D 7/06* (2013.01); *B05D 2203/20* (2013.01); *B27K 3/00* (2013.01); *B27K 3/50* (2013.01)
USPC .......................................... 427/345; 427/397

(58) Field of Classification Search
None
See application file for complete search history.

(56) References Cited

U.S. PATENT DOCUMENTS

| | | | | |
|---|---|---|---|---|
| 2,650,885 | A | * 9/1953 | Hudson ........................ | 427/335 |
| 3,657,412 | A | * 4/1972 | Reuther et al. ................ | 514/611 |
| 3,785,770 | A |   1/1974 | Hudson | |
| 3,967,011 | A | * 6/1976 | Dunn et al. ................... | 427/345 |
| 4,548,839 | A | * 10/1985 | Moldrup et al. .............. | 427/345 |
| 4,648,988 | A |   3/1987 | Van Duck et al. | |
| 5,209,886 | A |   5/1993 | Simons | |
| 5,990,143 | A | * 11/1999 | Ludwig et al. ............... | 514/383 |
| 6,123,795 | A |   9/2000 | Symons | |
| 6,231,651 | B1 | * 5/2001 | Schultz et al. ............. | 106/18.32 |
| 6,827,949 | B2 |   12/2004 | Yoshida et al. | |
| 2002/0128311 | A1 | * 9/2002 | Gironda et al. ............... | 514/528 |
| 2005/0025795 | A1 | * 2/2005 | DeLong et al. ............... | 424/405 |
| 2006/0112850 | A1 |   6/2006 | Zhang et al. | |
| 2007/0098750 | A1 | * 5/2007 | Bessette ....................... | 424/405 |
| 2007/0131136 | A1 | * 6/2007 | Zhang et al. ............... | 106/15.05 |
| 2007/0154393 | A1 |   7/2007 | Scharf et al. | |
| 2007/0227399 | A1 | * 10/2007 | Abou-Nemeh ............ | 106/15.05 |
| 2007/0258940 | A1 | * 11/2007 | Hamilton et al. .......... | 424/78.09 |

FOREIGN PATENT DOCUMENTS

| | | |
|---|---|---|
| CA | 2204119 | 5/1996 |
| JP | 7304609 A | 11/1995 |
| JP | 2000141317 | 5/2000 |
| NZ | 216318 | 2/1989 |
| WO | WO 97/45591 | 12/1997 |
| WO | WO 01/12901 | 2/2001 |
| WO | WO2008006714 | * 1/2008 |

OTHER PUBLICATIONS

International Search Report from PCT/NZ2009/000285, mailed May 27, 2010.
European Search Report from EP 09 83 8462.1, mailed May 23, 2012.
Further Examination Report in New Zealand Application No. 593327, dated May 29, 2014.

* cited by examiner

*Primary Examiner* — Erma Cameron
(74) *Attorney, Agent, or Firm* — Wolf, Greenfield & Sacks, P.C.

(57) ABSTRACT

This invention is related to a wood preservative composition comprising i) at least one active ingredient, and ii) a carrier system containing at least 10% w/w of a solvent selected from one or more ester compounds of the formula (I) wherein: R and R' are independently selected from Ci-Cβ-alkyl groups, and wherein the carbon chains of alkyl groups of 3 or more carbon atoms may be straight-chained or branched; and wherein the at least one active ingredient is substantially soluble in the earner system. The preservative compositions may be used to treat wood based materials, and the ester solvent may optionally be recovered following the treatment. Formula (I).

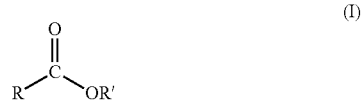

(I)

6 Claims, No Drawings

COMPOSITIONS FOR THE TREATMENT OF TIMBER AND OTHER WOOD SUBSTRATES

CROSS REFERENCE TO RELATED U.S. PATENT APPLICATIONS

The present application is a U.S. National Stage application based on International Application No. PCT/NZ2009/000285, filed Dec. 11, 2009, which claims priority to New Zealand Application No. 573574, filed Dec. 12, 2008.

FIELD OF THE INVENTION

The invention described herein relates to novel preservative compositions and treatments to enhance the long term durability of timber and other wood based materials.

BACKGROUND ART

Wood is not a naturally durable material and will deteriorate by insect and fungal attack if left exposed to the environment. No wood species is immune from such attack, although variations in durability may occur according to the chemical or physical nature of individual species.

Durability may be imparted by limiting access of food, moisture or air to the invading organisms and there are many examples of dry and coated wood that have remained intact over centuries.

Alternatively wood durability may be imparted by incorporation of chemicals into the wood structure, which may be toxic or indirectly active against the invaders, e.g. by affecting reproductive capacity. Such chemicals are termed wood preservatives.

In many cases, surface treatment with active chemicals is insufficient for wood preservation because subsequent processing or fabrication may expose fresh surfaces or promote new pathways for biological attack. Thus deep penetration of actives is preferred to simple envelope treatment. Robust wood preservative systems incorporate either aqueous or non-aqueous solvent carriers to transport active chemical ingredients to the interior of the wood.

Aqueous wood preservative systems containing copper, chromium and arsenic (CCA) have been used commercially for over 60 years and proved highly effective. However CCA and recent replacements, also based mainly on copper salts, require a costly redrying process after treatment. Also customer acceptance of preservatives containing toxic or heavy metals may be limited and copper and chromium salts are highly coloured rendering them unsuitable for use in appearance grade wood products.

Organic solvent systems for wood preservation include both non-volatile and volatile solvents. Non volatile solvents, such as creosote, have been in commercial use since the nineteenth century but issues related to cleanliness, odour and paintability of the treated wood have led to a decline in the use of such treatments.

In contrast, treatments based on volatile solvents, which evaporate from wood over periods measured in days, have increased considerably over the last 30 years in New Zealand, where there are currently about 20 plants using such treatments. The process known as LOSP (light organic solvent process) utilizes white spirit, a petroleum fraction, as carrier for the active ingredients. The composition of white spirit differs according to refinery source but typically, as supplied in New Zealand, comprises 50% paraffins, 25% naphthenes and 25% aromatic hydrocarbons, has a flashpoint of 38° C., and a distillation range from 150°-200° C.

The major LOSP formulations used commercially in NZ and in other countries may contain insecticides such as permethrin and/or fungicides such as iodo propyl butyl carbamate (IPBC), or triazole compounds, such as tebuconazole or propiconazole or tin compounds such as tri butyl tin naphthenate. Additionally LOSP formulations may incorporate water repellents, such as hydrocarbon resins and waxes and may require use of co-solvents to aid dissolution of the active ingredients or water repellents.

The advantages of LOSP treatments are the ability to impregnate wood with water insoluble active ingredients; there is little swelling or grain raise of the treated wood, and the process is cost competitive because there is no requirement for re-drying of the wood. These advantages allow the treatment process to be the final stage of timber production and timber mills therefore avoid creating wastes (sawdust, shavings, off-cuts) containing treatment chemicals.

The disadvantages of LOSP treatments relate to issues of health, safety and the environment. Release of LOSP solvent from the treated wood to atmosphere denotes that the process is a significant contributor of volatile organic compounds (VOC's). Some of the hundreds of individual compounds which constitute white spirit have suspected carcinogenic status and some have undefined toxicological properties. White spirit has a characteristic odour and workers may suffer headaches and other symptoms when handling freshly treated timber.

In addition the process step of waiting for most of the solvent to be evolved from the timber before painting may take several weeks or more in colder climates or where minimal airflow occurs across wood surfaces. Long holding periods cause manufacturing bottlenecks and impose increased working capital costs.

Adverse health, safety and environmental properties of LOSP treatments may be mitigated by incorporating solvent capture and recycle as part of the process. Heating of the timber is required to effect fast removal rates of this only moderately volatile white spirit solvent (boiling point 150°-200° C.) from deep inside the wood. However at elevated temperatures, particularly above 60° C., the resin and fatty acid extractives fraction of the wood becomes increasingly soluble in the solvent, leading to unsightly "resin bleed" at the surface of the wood.

NZ Patent 535897 relates to a LOSP solvent recovery process based on radiofrequency (RF) heating of the wood to temperatures between 40° and 65° C. The ability of such a process to deal with resin bleed issues outlined above is not disclosed.

Alternative recoverable non-aqueous solvents are outlined by Richardson p 83 (*Wood Preservation by Barry A Richardson, pub, Taylor and Francis,* 1993) include LPG or Butane, known as the Drilon or Cellon Process and methylene chloride, known as the Dow process. In the case of the Cellon or Drilon process, where vacuum recovery is practised, the potentially hazardous conditions require difficult and high energy adiabatic restrictions, which have deterred commercialization. Methylene chloride use has also a number of health and safety concerns and the use of steam distillation recovery in the Dow process has a significant energy cost.

These limitations have prevented any widespread adoption of commercial development of solvent recovery for any of the organic solvent carrier wood preservation treatments.

SUMMARY OF THE INVENTION

In one aspect, the invention provides a wood preservative composition comprising:

i) at least one active ingredient;
ii) a carrier system containing at least 10% w/w of a solvent selected from one or more ester compounds of the formula (I):

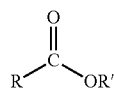

(I)

wherein R and R' are independently selected from $C_1$-$C_6$-alkyl groups, and wherein the carbon chains of alkyl groups of 3 or more carbon atoms may be straight-chained or branched; and wherein the at least one active ingredient is substantially soluble in the carrier system.

In a preferred embodiment, at least one of the ester compounds of the formula (I) is selected from n-propyl ethanoate, tertiary butyl ethanoate, and n-propyl propanoate.

The carrier system may optionally comprise at least one other solvent in addition to the solvent selected from one or more ester compounds of the formula (I). For example, the carrier system may optionally comprise white spirits in addition to the solvent selected from one or more ester compounds of the formula (I).

In another preferred embodiment, the at least one active ingredient is selected from permethrin, propiconazole, tebuconazole or a mixture of two or more thereof.

In still another preferred embodiment, the wood preservative composition comprises at least one co-ingredient that is substantially soluble in the carrier system.

In another aspect, the invention provides a method of preserving a wood based material comprising applying a wood preservative composition of the present invention to the wood based material.

In a preferred embodiment, the method comprises the step of recovering the solvent or solvents from the wood based material after applying the wood preservative composition of the invention to the wood based material.

DETAILED DESCRIPTION OF THE INVENTION

It has been discovered that certain lower molecular weight carboxylic acid ester compounds (hereafter referred to as ester compounds or esters) may be used as solvents in wood preservative compositions and methods.

In one aspect, the present invention provides a wood preservative composition comprising:
i) at least one active ingredient;
ii) a carrier system containing at least 10% w/w of a solvent selected from one or more ester compounds;
wherein the at least one active ingredient is substantially soluble in the carrier system.

The range and scope of ester Compounds that may be used in the present invention include ester compounds of the formula (I):

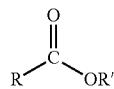

(I)

wherein R and R' are independently selected from $C_1$-$C_6$-alkyl groups, and wherein the carbon chains of alkyl groups of 3 or more carbon atoms may be straight-chained or branched.

Particularly preferred ester compounds of the formula (I) that may be used in the present invention include n-propyl ethanoate, tertiary butyl ethanoate, and n-propyl propanoate.

The carrier system may optionally comprise at least one other solvent in addition to the solvent selected from one or more ester compounds of the formula (I). For example, the carrier system may optionally comprise white spirits in addition to the solvent selected from one or more ester compounds of the formula (I).

In another preferred embodiment, the at least one active ingredient is selected from permethrin, propiconazole, tebuconazole or a mixture of two or more thereof.

In still another preferred embodiment, the wood preservative composition comprises at least one co-ingredient that is substantially soluble in the carrier system. Co-ingredients may include, for example water repellents and fire retardants.

In another aspect, the invention provides a method of preserving a wood based material comprising applying a wood preservative composition of the present invention to the wood based material.

In a preferred embodiment, the method comprises the step of recovering the solvent or solvents from the wood based material after applying the wood preservative composition of the invention to the wood based material.

Preferably the ester compounds of the formula (I) have at least some of the following characteristics: characteristics which allow formulation of active ingredients and co ingredients, such as water repellents and fire retardants; suitable health, safety and environmental properties; ability to penetrate wood (at least sapwood); high recovery levels from wood; overall favourable processing cost structure for the treatment and recovery processes; and minimal wood dimensional changes during treatment or recovery.

It is particularly preferred that the ester compounds of the formula (I) are more readily evolved by wood based materials than white spirits.

On the basis of cost the ethanoate ester compounds are generally preferred as they are bulk commodities with many industrial uses as solvents for paints and resins etc.

The toxicity profiles of all of the ester compounds of this invention are particularly favourable compared to white spirit. Many of the esters including n-propyl ethanoate and butyl ethanoates are naturally occurring compounds in fruits such as apples, grapes, pineapples etc., and many of the ester compounds are used as flavour additives. Toxicity considerations constitute important advantages of the compounds of this invention.

On the basis of lower flammability the higher molecular weight esters of the formula (I) may be preferred. Esters such as ethyl ethanoate and butyl methanoate, have flash points of 23° C. or less and therefore are classed as Class 3.1B Flammable Liquids under the NZ HSNO Regulations. This may impose higher costs of plant design compared to other esters such as pentyl methanoate and n-propyl propanoate, which are Class 3.1C Flammable Liquids.

On the basis of odour some esters may be preferred. For instance iso-butyl propanoate is described as having the odour of rum essence and hexyl ethanoate as having peach essence. However, odour perceptions and odour threshold levels vary widely between observers and it would be preferred that the treated wood in service has undetectable or minimal enduring odour.

On the basis of high water miscibility, low molecular weight esters such as methyl ethanoate (22% soluble) and ethyl ethanoate (7.4% soluble) may not be preferred as some water is also condensed during the recovery process. Therefore highly water miscible solvents would require a costly water/ester separation step in the recovery process.

On the basis of solubility of various actives and co-ingredients, such as water repellents and fire retardants, etc, there are no obvious preferences among the range of esters encompassed in this invention. Published data such as the Hansen solubility coefficients are not particularly useful predictors in this research, as apart from a general decrease in polar bonding character for higher molecular weight esters (an obvious characteristic) the non-polar and hydrogen bonding coefficients for the various esters are reasonably similar.

On the basis of formulation stability it can be predicted that highly acidic or highly alkaline ingredients would not be preferred, as such materials may lead to partial or complete breakdown of the ester. Therefore the fungicide sodium orthophenyl phenate (pH=13) may not be a suitable component of the formulations of this invention. Also for stability reasons, reducing agents such as phosphite or sulphite compounds would not be suitable, but such compounds are rarely used in wood preservative formulations.

The suitability of individual esters with respect to ease of recovery of solvent, swelling of treated wood, ability to impregnate wood, and ability to provide stable compositions containing suitable actives and co-ingredients of wood preservative formulations may be ascertained by experimentation. Such experimentation forms the basis of the following examples, including:

Examples 1 and 2, in which it is shown that ester solvents are more readily uptaken and evolved by timber compared to white spirit and apart from ethyl ethanoate, cause only minor swelling of wood.

Example 3, in which it is shown that ester solvents may be formulated with the active ingredients and co-ingredients of wood preservatives.

Example 4, in which it is shown that solvent recovery rates from timber treated with esters, such as n-propyl ethanoate, n-propyl propanoate and tertiary butyl ethanoate are much higher compared to timber treated with white spirit.

Example 5, in which a comparison of formulations containing tributyl tin naphthenate showed that n-propyl ethanoate compared favourably to white spirit with regards to rate of solvent recovery. The degree of impregnation of the active ingredient was acceptable in both cases.

Example 6, in which the impregnation and solvent recovery characteristics of white spirit and n-propyl ethanoate are compared on plywood to show that the invention also has application to wood composite based materials.

To carry out the experimentation described in the examples it was necessary to construct a pilot plant for recovery of solvent vapours from treated wood. The plant consisted of a reaction chamber 900 mm×125 mm×125 mm in which recycled vapours delivered by a side channel blower were allowed to pass over the surfaces of filleted pieces of treated timber, with velocities up to 6 m/second. A portion of the recycled vapours (up to 30 L/minute) was diverted through a 15 m coil (9 mm diameter), externally cooled with ice, and the condensed solvent was collected in an ice cooled receiver and the stripped vapours returned to the main flow.

The plant was constructed without any external heat source, although the recycled air temperature continuously increased from the mechanical energy of the blower and temperature increases of the inlet air to the reactor from 15° C. at the start of reaction to 35° C. at the end of the three hour reaction period were observed. Temperatures of the exit air from the cooling coil ranged from 7°-10° C.

The recovery plant was also constructed without vacuum capability and without provision to absorb the final concentrations of solvent vapours from the atmosphere, for instance, in an activated carbon bed. Although external heating, vacuum capability and solvent absorption may be useful provisions in the attainment of maximum possible recoveries of solvent, the pilot plant as constructed was sufficient to meet the needs of this experimentation. As shown in the following examples, high degrees of solvent recovery were attainable in the pilot plant and differentiation between the recovery capability of the various solvents and white spirit was possible.

The experimental work outlined in the examples has assisted in identification of several esters which may have particular advantages in some industrial applications. These exemplified advantages should not be interpreted as limiting the range of ester compounds defined in the invention, or the scope of the invention in any way.

For example, the ester n-propyl ethanoate is preferred because of its low cost and the experimental work has shown good recovery rates. The chemical also has a good toxicological profile, being a naturally occurring compound in many fruits, such as apples and pears, and n-propyl ethanoate is added to wine in some countries.

The ester tertiary butyl ethanoate is also preferred because of the special status accorded to it (by the US Environmental Protection Agency) as a non-VOC (volatile organic compound). Only a few solvents have this exempt VOC status and thus substitution of tertiary butyl ethanoate for white spirits in solvent borne products has clear environmental advantages. Very good recovery rates were also achieved with tertiary butyl ethanoate.

The ester n-propyl propanoate is also preferred because of its flashpoint of 24° C. Compounds with flashpoints greater than 23° C. belong to the same class of 3.1C flammables (NZ HSNO Regulations) as white spirit. Therefore capital cost savings may accrue to existing LOSP operations which may convert to using n-propyl propanoate without modification of fire safety features of the plants. Although recovery rates were not as high as with some of the other esters, n-propyl propanoate has a very pleasant odour and any residual solvent in the wood may be more acceptable than white spirit.

In some cases mixtures of ester products may be advantageously employed. If for instance the first ester of a mixture has a flash point of under 23° C., it may be mixed with a second ester of higher flashpoint in order to maintain the flashpoint of the mixture above 23° C., and thus avoid the more demanding requirements of Class 3.1B regulations.

In some cases it may be advantageous to mix esters with white spirit or other lower cost solvents. The white spirit component of such formulations may act as a sacrificial compound which disproportionately remains in the wood after solvent recovery proceeds to release the major amount of ester. There may also be some advantages in recovery rates by the azeotropic distillation of such mixtures and the blending of white spirit with esters also provides potential for increased flashpoints of the formulations.

In the blending of esters with other solvents it is envisaged that the ester component would be a major component of the mixture, preferably greater than 50%, and thus contribute significantly to the enhanced recovery characteristics of the solvent fluid. It is considered unlikely that compositions with total ester contents of less than 10% of total solvent content would retain the essence of this invention.

The formulation studies have shown good solubilisation of tebuconazole, propiconazole, tributyl tin naphthenate, resins, waxes, IPBC, and permethrin in the esters of the invention. These components allow formulation of the currently used LOSP compositions using esters as replacement for white spirit. Ester formulations may be either formulated as ready-for-use solutions or alternatively as concentrates where say an 8:1 (or higher) concentrate is delivered to the production site where blending with recovered solvent takes place. The degree of concentration of the actives may depend on solvent recovery efficiencies. Transport cost savings form an important consideration in defining the advantages of this invention.

EXAMPLES

Example 1

Preliminary Evaluation of the Impregnation and Evolution Characteristics of N-Propyl Ethanoate To demonstrate the potential for solvent recovery from treated wood of n-propyl ethanoate the following experiment was carried out.
  (a) Two pieces of untreated kiln dried *Pinus radiata*, dimensions 90 mm×45 mm×360 mm were dipped in a solution of n-propyl ethanoate for two minutes. An average uptake of 54 g indicated a corresponding uptake of 36 L/m$^3$ which is similar to commercial LOSP treatments. The wood pieces were sealed in polyethylene bags and left to equilibrate for two days. After equilibration the pieces were stored in a sheltered outside environment to allow solvent loss by evaporation. After two days the wood was inspected and a faint or barely perceptible odour of propyl ethanoate was detected. After a further 24 hours exposure no odour of propyl ethanoate was detectible in the wood.
  (b) A corresponding experiment was carried out using white spirit instead of n-propyl ethanoate. The average white spirit uptake was 32 L/m$^3$ and after five days the characteristic odour of white spirit was still detectable.

The experiment confirms the relatively high volatility of n-propyl ethanoate compared to white spirit. The odour threshold of n-propyl ethanoate is 2 ml/m$^3$ and therefore the absence of perceptible odour at the surface of the wood, suggests essentially 100% evolution of the chemical.

The rapid evolution of n-propyl ethanoate from the wood within two days demonstrates a major cost advantage of the invention compared to current used white spirit formulations where waiting periods of 5-10 days are required to evolve sufficient solvent to allow wood priming or painting.

Example 2

Comparison of Impregnation, Evolution and Swelling Characteristics of Ester Solvents Preliminary tests on *Pinus radiata* as indicated in Example 1 showed that ester solvents may have suitable characteristics for wood treatment processes which include recovery of solvent. Fast grown, low density Radiata is considered easily penetrable by solvents and it is of interest to confirm that these solvents would have application to other coniferous species.

The wood species chosen for this study was *Pinus ponderosa* from Oregon State USA, which as indicated by the narrow growth ring spacings, bad relatively slow growth compared to NZ softwoods. Using white spirits as a base for comparison, wood treatments with four different esters were carried out, to yield information on ease of uptake, rate of solvent loss and degree of swelling.

Wood pieces 38.6 mm×38.6 mm×72 mm (long) were selected containing well defined tangential and radial direction sawn faces. The pieces were submerged for periods of two to four days in the various solvents until uptakes in the range 115-130 L/m$^3$ were achieved. The ester solvents chosen were ethyl ethanoate, n-propyl ethanoate, n-butyl ethanoate and iso-pentyl ethanoate. Three wood pieces per solvent treatment were used for the study.

After the desired uptakes were obtained, the wood pieces were placed in sealed containers for a further two to four days to ensure good diffusion of the solvent throughout the wood. At that stage the pieces were re-measured to determine dimensional swelling and re-weighed prior to commencement of trials of solvent evolution rates.

The wood pieces were placed on plastic bearers allowing good access of air to all surfaces and situated in a dedicated room with no external airflow. Air temperatures in the room were mainly in the range 17-22° C.

The wood pieces were re-weighed daily to determine weight loss rates for the various solvents. In addition to the four ester solvents, two similar treatments using white spirits and water were used as references.

The treatments using water, ethyl ethanoate and n-propyl ethanoate achieved uptakes shown in Table 1 within two days of soaking. The slowest uptake rates occurred with the iso-pentyl ethanoate and white spirits treatments which required four days soaking to achieve the desired uptakes. Tangential, radial and volumetric swellings for the treatments are compared in Table 1.

TABLE 1

Comparison of Tangential, Radial and Volumetric Swellings for the Various Treatments.

| Treatment | Uptake (L/m$^3$) | Tangential Swelling (%) | Radial Swelling (%) | Volumetric* Swelling (%) |
|---|---|---|---|---|
| Ethyl Ethanoate | 130 | 3.7 | 0.8 | 4.5 |
| n-Propyl Ethanoate | 128 | 0.9 | 0.5 | 1.4 |
| n-Butyl Ethanoate | 130 | 0.7 | 0.2 | 0.9 |
| iso-Pentyl Ethanoate | 115 | 0.5 | 0.3 | 0.8 |
| White Spirits | 122 | 0.4 | 0.2 | 0.6 |
| Water | 147 | 3.3 | 2.6 | 6.0 |

The ethyl ethanoate treatment was accompanied by significant dimensional increases of the wood (volumetric swelling 4.5%) but not as high as the water treatment (volumetric swelling=6.0%). The other ester treatments resulted in volumetric swellings in the range 0.8% to 1.4%, slightly higher than the white spirits treatment (swelling=0.6%)

As indicated in the table, significant swelling was associated with ethyl ethanoate. Lower swelling was associated with the other esters which are more hydrophobic than ethyl ethanoate. The lowest swelling was associated with the white spirits treatment. However there are high measurement errors associated where dimensional increases are less than 1% and these apparent differences may not be significant in practice, where solvent uptakes are much lower.

Comparison of the rates of evaporation of the various solvents is shown in Table 2.

TABLE 2

Comparison of Solvent Evaporation Rates.

| Treatment | Uptake (L/m³) | % Solvent Remaining in Wood | | |
|---|---|---|---|---|
| | | After 24 h | After 48 h | After 72 h |
| Ethyl Ethanoate | 130 | 3.8 | 0 | 0 |
| n-Propyl Ethanoate | 128 | 6.0 | 0.8 | 0 |
| n-Butyl Ethanoate | 130 | 6.9 | 3.1 | 0.8 |
| iso-Pentyl Ethanoate | 115 | 7.0 | 4.3 | 1.7 |
| White Spirits | 122 | 12.2 | 9.0 | 3.3 |
| Water | 147 | 22.4 | 14.3 | 12.2 |

The results showed that virtually all ethyl and n-propyl acetate solvent was removed from the wood within 48 h of storage. The n-butyl ethanoate and iso-pentyl ethanoate treatments showed less solvent volatility and the rate of removal of white spirits was slower than all the ethanoate treatments.

The fastest evaporation rates occurred with ethyl ethanoate and n-propyl ethanoate with essentially all solvent released within two to three days of wood storage. N-Butyl ethanoate and iso-pentyl ethanoate treated samples had slower rates of evolution but still faster than the wood pieces containing white spirits.

These results indicate that ethyl ethanoate, may be a lesser preferred ester for the treatment of wood because of wood swelling. However use of ethyl ethanoate has not been discounted as a component of a mixed solvent formulation, where only minor swelling is contributed and advantages accrue from the high volatility of the chemical.

Example 3

Formulation Properties of Ester Solvents

As indicated by their industrial usages in coatings formulations, the esters have good solvency characteristics. However there is no reported information on the abilities of such compounds to solubilise the range of biocides and co-ingredients used as wood preservatives. There are thousands of compounds which have been identified as active against fungi, insects or bacteria which have potential application to the preservation of timber and other wood substrates.

The formulation of active ingredients and co-ingredients of wood preservative formulations by the ester compounds of the invention are only limited by (a) dissolution power—for instance the compound chlorothalonil has been found in this research to be less than 1% soluble in propyl and butyl ethanoate and therefore chlorothalonil may not be a useful component of this invention. This restriction is not serious as the only use of chlorothalonil in the industry is for topical treatments (antisapstain products); (b) products that hydrolyse esters—for instance highly acidic or basic products may hydrolyse the ester into alcohol and carboxylic acid components. Therefore sodium orthophenylphenate (pH=13) may not be a suitable component of this invention (again this chemical is only used for antisapstain treatments); and (c) reducing agents, which may include phosphite and sulphite compounds, although such compounds are not usually considered as components of wood preservatives.

The aforementioned limitations exclude some potential wood preservatives but it is more useful to determine whether specific active ingredients, currently used in the industry, may be formulated by the esters of this invention.

The major LOSP formulations used commercially in NZ may contain insecticides such as permethrin and/or fungicides such as iodo propyl butyl carbamate (IPBC), or triazole compounds, such as tebuconazole or propiconazole. Additionally LOSP formulations may incorporate water repellents, such as hydrocarbon resins and waxes and may require use of co-solvents to aid dissolution of the active ingredients or water repellents.

As an example of this invention, the following formulation was prepared: (parts by weight)
Permethrin 3.7%, Propiconazole 5.5%, Tebuconazole 5.5%, Hydrocarbon resin (Petrosin 120) 18.9%, Stearyl Laurate 2.6%, n-Propyl ethanoate 63.8%.

The quantities of active ingredients and water repellents in the prepared sample are approximately eight times the quantities required for a working strength commercial formulation used to treat wood to the H3 Hazard Class in NZ. The sample stored in a sealed container at ambient temperatures over six months showed no signs of cloudiness or instability. A subsample diluted to working strength with n-propyl ethanoate also showed no formulation instability.

Further formulation tests were carried out to ascertain if the fungicide IPBC (iodo propyl butyl carbamate, CAS No 55406-53-6) was soluble in ester compounds of formula (I). Preparations of IPBC (5% by weight) in n-propyl ethanoate, n-propyl propanoate, n-butyl ethanoate, iso-pentyl ethanoate and tertiary butyl ethanoate produced clear stable solutions in all cases. The excellent solubility of IPBC in ester solvents is a major advantage over white spirit based LOSP formulations, which require additions of co-solvents to solubilise IPBC at levels required for commercial formulations.

Example 4

Comparative Recovery Rates of Timber Impregnated with Ester Solvents

Timber pieces 90 mm×18 mm×455 mm were impregnated with three ester solvents and one sample of white spirit. The solvents included n-propyl ethanoate, n-propyl propanoate, and tertiary butyl ethanoate. Seven timber pieces were included in each trial and solvent uptakes ranged from 27 to 39 L /m3.

The treated timber pieces were wrapped in polyethylene for 18-20 h to ensure good diffusion of solvent throughout the wood before removal of solvent in the solvent recovery plant. Prior to commencing solvent recovery the timber pieces were reweighed. At hourly intervals over the three hour recovery period the timber pieces were removed from the recovery chamber, quickly reweighed and returned to the chamber.

During recovery, solvent and water were collected in the receiver and the total solvent collected each hour was recorded. The collected quantities of solvent for each of the treatments, expressed as percentage w/w of solvent used are shown in Table 3.

TABLE 3

Recovered Solvent Percentages for the Solvent Treatments

| | Total Solvent Recovered (%) | | |
|---|---|---|---|
| | After 1 h | After 2 h | After 3 h |
| White Spirit | 10.8 | 22.6 | 28.0 |
| N-propyl propanoate | 25.3 | 34.5 | 38.7 |

TABLE 3-continued

Recovered Solvent Percentages for the Solvent Treatments

| | Total Solvent Recovered (%) | | |
|---|---|---|---|
| | After 1 h | After 2 h | After 3 h |
| N-propyl ethanoate | 32.2 | 41.7 | 46.1 |
| Tert-butyl ethanoate | 35.8 | 52.5 | 58.3 |

The quantities of solvent (and water) removed from the wood are significantly higher than actually reclaimed in the receiver of the pilot plant. This discrepancy is most obvious in the first comparison made after one hour of recovery, and is due mainly to unrecovered liquid which wets the cooler surfaces of the recovery system. Other losses may occur during removal of wood for weighing, leaks, and non condensed solvent in the atmosphere at the conclusion.

The discrepancy between weight loss of the wood and liquid collected apportioned according to the relative amounts of water and solvent actually collected, leads to corrected expressions of the percentages of solvent removed from the timber as shown in Table 4.

TABLE 4

Percentage Solvent Removed from the Timber.

| | % Solvent Removed from the Timber | | |
|---|---|---|---|
| | After 1 h | After 2 h | After 3 h |
| White Spirit | 20.0 | 32.1 | 37.7 |
| N-propyl propanoate | 31.7 | 43.7 | 50.3 |
| N-propyl ethanoate | 42.7 | 55.5 | 60.0 |
| Tert-butyl ethanoate | 47.5 | 65.0 | 73.3 |

The data in Tables 3 and 4 demonstrate the inherent advantages of the ester solvents, compared to white spirit, in terms of the much higher percentage recoveries of the carrier solvents. Analysis of samples of the collected solvents by fourier transform infrared spectroscopy (FTIR) did not reveal any quantities of other volatile compounds.

The N-propyl ethanoate and N-propyl propanoate treated wood pieces had only mildly detectable odour when removed from the chamber at the end of the trials. When observed the following day the odour was not detectable. The odour of tertiary butyl ethanoate treated pieces was barely detectable upon removal from the chamber indicating the data in Tables 3 and 4 may have understated the quantities of solvent removal from the wood. In comparison, the characteristic and unpleasant odour of white spirits from the treated pieces was still observable two weeks after the recovery trial.

Therefore this trial also demonstrated that one of the major disadvantages of worker discomfort in downstream usage of white spirit based treatments, such as frame and truss operations, could potentially, be overcome by these ester based treatments.

Example 5

Comparison of Wood Impregnation and Recovery of H3 Type Formulations Based on White Spirit and N-Propyl Ethanoate (a) A LOSP (white spirit based) preservative solution was prepared of similar composition to that used in the NZ treatment industry and based on the active ingredient tributyl tin naphthenate. The concentrations per litre of fluid were tributyl tin naphthenate 85 g, permethrin 5 g, IPBC 1.2 g, hydrocarbon resin (Petrosin 120) 35 g, stearyl laurate 8 g, butanol 5 g and white spirit 680 g (balance to 1 L).

Timber pieces (*Pinus Radiata*) 600 mm×90 mm×18 mm were end sealed (PVA emulsion) then treated in a pilot LOSP plant where seven pieces per charge were impregnated with the above fluid at a vacuum of −30 kPA, held for 10 seconds, followed by a further soak period of 10 seconds at atmospheric pressure before drainage. After draining the treatment chamber a final vacuum of −85 kPa was held for 15 minutes.

The timber was re-weighed to determine fluid uptakes and transferred to the pilot recovery plant to commence recovery. At the end of the solvent recovery trial the timber was reweighed and conditioned for 24 h prior to examination of cross sections for determination of the penetration of the tin compound.

(b) A similar formulation was produced substituting n-propyl ethanoate for the white spirit and butanol in (a) above and the impregnations and recovery conditions were repeated.

The results for the impregnations showed an average uptake of 36 L/m$^3$ for the white spirit formulation and 46 L/m$^3$ uptake for the n-propyl ethanoate formulation. This suggests that propyl ethanoate has at least equal if not greater ability than white spirit to penetrate the wood matrix.

After 3 h recovery, 33.6% of the white spirit was removed from the wood. The comparative recovery of n-propyl ethanoate over the same period was 53.2%. This relativity of recovery rates is similar to the earlier trials using solvent only, outlined in Example 4.

Spot tests for tin in cross sections showed complete penetration of sapwood for both the white spirit and n-propyl ethanoate treatments.

Example 6

Comparison of the Impregnation of Plywood with N-Propyl Ethanoate and White Spirit Application of this invention to the impregnation and recovery of ester solvents from other wood based materials was demonstrated on plywood. Penetration of plywood is less easily achieved because of the relatively impermeable interlayer gluelines.

Pieces of 6 ply, 18 mm thick plywood, cut into strips 800 mm×120 mm were sealed (one end and both sides) for impregnation with the TBTN containing formulations containing white spirit or n-propyl ethanoate, outlined in Example 5. Impregnation was carried out by a similar schedule outlined in Example 5 except for an extended soak period at atmospheric pressure to achieve higher uptakes normally required to achieve satisfactory penetration of plywood. Similar uptakes of 43.5 L/m3 for white spirit and 40.9 L/m3 for n-propyl ethanoate were achieved.

After treatment recovery trials were carried out as per the previous examples. After 3 h recovery 24.4% of the white spirit was removed from the wood, whereas over the same period 58.1% of the n-propyl ethanoate was recovered. This again confirms the enhanced recovery rates achievable with the ester solvent.

After recovery, cross sections of the plywood were examined with a spot test for tin (PAN indicator) to determine the degree of impregnation. A general gauge of reasonable impregnation is indicated if the inner two plys are fully positive on the spot test on a cross section cut 150 mm from the unsealed end. This was achieved for both solvents. Therefore it is considered that the ester based technology is also applicable to other wood based materials.

The invention claimed is:

1. A method of preserving a wood based material comprising:
   a) impregnating the wood based material with a wood preservative composition comprising:
      i) at least one active ingredient;
      ii) an organic carrier system containing at least 10% tert-butyl ethanoate by weight,
      wherein the at least one active ingredient is substantially soluble in the organic carrier system;
   b) recovering the tert-butyl ethanoate from the wood based material after impregnation.

2. A method according to claim 1, wherein the carrier system comprises at least one other solvent in addition to tert-butyl ethanoate.

3. A method according to claim 1, wherein the carrier system comprises white spirits in addition to the tert-butyl ethanoate.

4. A method according to claim 1, wherein the at least one active ingredient is selected from permethrin, propiconazole, tebuconazole or a mixture of two or more thereof.

5. A method according to claim 1, comprising at least one co-ingredient that is substantially soluble in the carrier system.

6. A method according to claim 2, wherein the at least one other solvent is selected from the group consisting of n-propyl ethanoate, tertiary butyl ethanoate, and n-propyl prop anoate.

* * * * *